United States Patent [19]

Kamiya et al.

[11] 4,305,937
[45] * Dec. 15, 1981

[54] 2-LOWER ALKYL-7-SUBSTITUTED-2 OR 3-CEPHEM-4-CARBOXYLIC ACID COMPOUNDS AND ANTIBACTERIAL PHARMACEUTICAL COMPOSITIONS CONTAINING THEM

[75] Inventors: Takashi Kamiya, Suita; Takao Takaya, Kawanishi, both of Japan

[73] Assignee: Fujisawa Pharmaceutical Co., Ltd., Osaka, Japan

[*] Notice: The portion of the term of this patent subsequent to May 1, 1996, has been disclaimed.

[21] Appl. No.: 64,761

[22] Filed: Aug. 8, 1979

[30] Foreign Application Priority Data

Aug. 17, 1978 [GB] United Kingdom ............. 33766/78

[51] Int. Cl.$^3$ ................ A61K 31/545; C07D 501/20; C07D 501/60
[52] U.S. Cl. .................... 424/246; 544/17; 544/22; 548/194; 548/195
[58] Field of Search .......... 544/22; 424/246; 546/17

[56] References Cited

U.S. PATENT DOCUMENTS

| | | | |
|---|---|---|---|
| 3,660,396 | 5/1972 | Wright | 544/30 |
| 3,719,672 | 3/1973 | Heusler et al. | 544/30 |
| 3,883,517 | 5/1975 | Heusler et al. | 544/30 |
| 4,024,133 | 5/1977 | Cook et al. | 424/246 X |
| 4,098,888 | 7/1978 | Ochiai et al. | 424/246 |
| 4,113,940 | 9/1978 | Kamiya et al. | 424/246 |
| 4,152,432 | 5/1979 | Heymes et al. | 424/246 |
| 4,152,433 | 5/1979 | Kamiya et al. | 424/246 |
| 4,166,115 | 8/1979 | Takaya et al. | 424/246 |
| 4,191,762 | 3/1980 | Kamiya et al. | 424/246 |

FOREIGN PATENT DOCUMENTS 2461933 7/1975 Fed. Rep. of Germany .

Primary Examiner—Donald G. Daus
Assistant Examiner—Diana G. Rivers
Attorney, Agent, or Firm—Oblon, Fisher, Spivak, McClelland & Maier

[57] ABSTRACT

A compound of the formula:

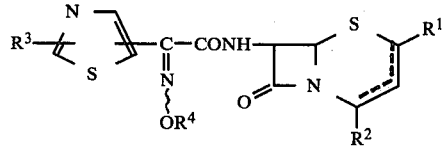

wherein $R^1$ is lower alkyl, $R^2$ is carboxy or protected carboxy, $R^3$ is amino or protected amino and $R^4$ is lower alkyl substituted by halogen or a lower unsaturated aliphatic group, and pharmaceutically acceptable salts thereof.

9 Claims, No Drawings

2-LOWER ALKYL-7-SUBSTITUTED-2 OR 3-CEPHEM-4-CARBOXYLIC ACID COMPOUNDS AND ANTIBACTERIAL PHARMACEUTICAL COMPOSITIONS CONTAINING THEM

The present invention relates to new 2-lower alkyl-7-substituted-2 or 3-cephem-4-carboxylic acid compounds and pharmaceutically acceptable salts thereof. More particularly, it relates to new 2-lower alkyl-7-substituted-2 or 3-cephem-4-carboxylic acid compounds and pharmaceutically acceptable salts thereof which have antimicrobial activities and to process for the preparation thereof, to pharmaceutical composition comprising the same, and to a method of using the same therapeutically in the treatment of infectious diseases in human being and animals.

Accordingly, it is one object of the present invention to provide 2-lower alkyl-7-substituted-2 or 3-cephem-4-carboxylic acid compounds and pharmaceutically acceptable salts thereof, which are active against a number of pathogenic microorganisms.

Another object of the present invention is to provide processes for the preparation of 2-lower alkyl-7-substituted-2 or 3-cephem-4-carboxylic acid compounds and pharmaceutically acceptable salts thereof.

A further object of the present invention is to provide pharmaceutical composition comprising, as active ingredients, said 2-lower alkyl-7-substituted-2 or 3-cephem-4-carboxylic acid compounds and pharmaceutically acceptable salts thereof.

Still further object of the present invention is to provide a method for the treatment of infectious diseases caused by pathogenic bacteria in human being and animals.

The object 2-lower alkyl-7-substituted-2 or 3-cephem-4-carboxylic acid compounds are novel and can be represented by the following general formula (I).

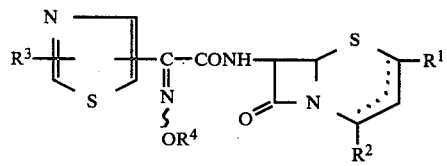

wherein
  $R^1$ is lower alkyl,
  $R^2$ is carboxy or a protected carboxy group,
  $R^3$ is amino or a protected amino group and
  $R^4$ is lower alkyl having halogen atom(s) or lower unsaturated aliphatic group.

According to the present invention, the 2-lower alkyl-7-substituted-2 or 3-cephem-4-carboxylic acid compounds (I) can be prepared by the processes which are illustrated by the following schemes.

Process 1.

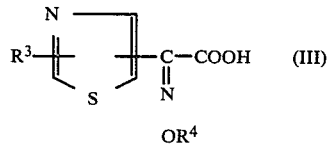

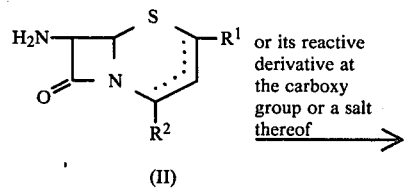

or its reactive derivative at the amino group or a salt thereof

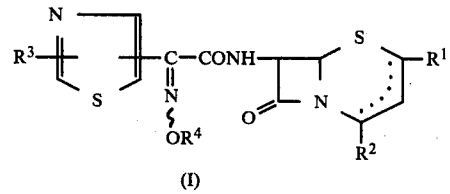

or a salt thereof

Process 2.

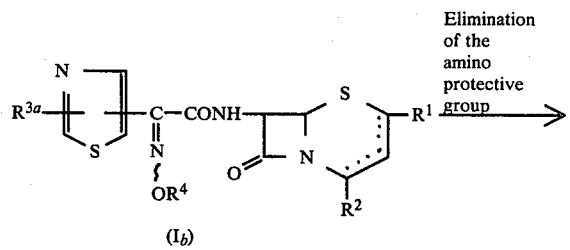

Elimination of the amino protective group or a salt thereof

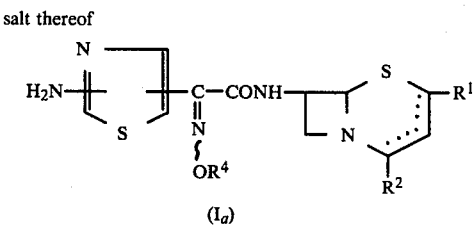

or a salt thereof wherein
  $R^1$, $R^2$, $R^3$ and $R^4$ are each as defined above, and
  $R^{3a}$ is a protected amino group.

The starting compound (II) in the present invention can be prepared according to the methods described in W. German Offenlegungsschrift No. 2,412,513.

Among the starting compounds (III) in the present invention, novel compounds can be prepared by the processes which are illustrated by the following schemes.

Method 1

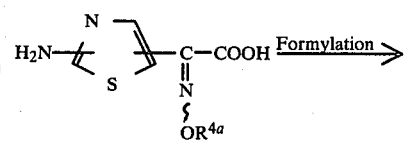

or its reactive derivative at the amino group or a salt thereof

-continued

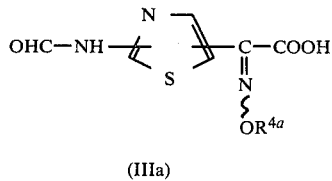

(IIIa)

or a salt therof

Method 2

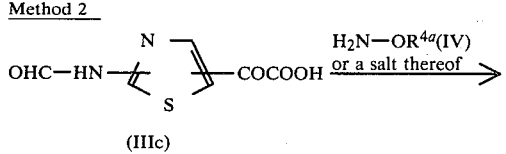

(IIIc)

or a salt thereof

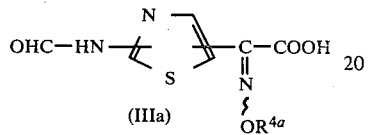

(IIIa)

or a salt thereof wherein $R^{4a}$ is lower unsaturated aliphatic group.

Regarding the object compounds (I) and (Ia)–(Ib) and the starting compounds (III), it is to be understood that they include tautomeric isomers. That is, in case that the group of the formula:

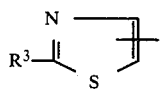

($R^3$ is as defined above) is contained in the molecules of said object and starting compounds, said group of the formula can also be alternatively represented by its tautomeric formula:

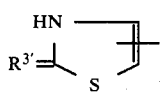

($R^{3'}$ is imino or a protected imino group). That is, the both of said groups are in the state of equilibrium each other and such tautomerism can be represented by the following equilibrium.

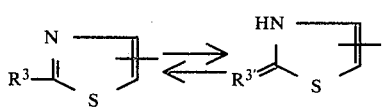

wherein $R^3$ and $R^{3'}$ are each as defined above.

These types of tautomerism between the amino-compound and the corresponding imino-compound as stated above have been well known in the literature, and it is obvious to be skilled in the arts that both of the tautomeric isomers are easily convertible reciprocally and are included within the same category of the compound per se. Accordingly, the both of the tautomeric forms of the object compounds (I) and (Ia)–(Ib) and the starting compound (III) are clearly included within the scope of the present invention. In the present specification and claims, the object and starting compounds including the group of such tautomeric isomers are represented by using one of the expressions therefor, that is the formula:

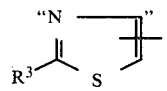

only for the convenient sake.

Furthermore, regarding the object compounds (I) and (Ia)–(Ib) and the starting compounds (III), it is to be understood that said object and starting compounds include syn isomer, and anti isomer and a mixture thereof, which can be optionally obtained as syn isomer or anti isomer or a mixture thereof. Accordingly, in this specification, syn isomer means one geometrical isomer having the partial structure represented by the following formula:

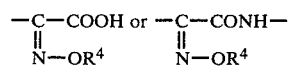

and anti isomer means the other geometrical isomer having the partial structure represented by the following formula:

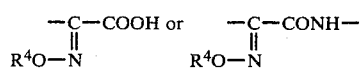

wherein $R^4$ is as defined above.

Suitable pharmaceutically acceptable salts of the object compounds (I) are conventional non-toxic salts and include a metal salt such as an alkali metal salt (e.g., sodium salt, potassium salt, etc.) and an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, N,N'-dibenzylethylenediamine salt, etc.), an organic acid salt (e.g., acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g., arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "lower alkyl" may include methyl, ethyl, propyl, isopropyl, butyl, pentyl, hexyl and the like.

Suitable "lower alkyl having halogen atom(s)" may include lower alkyl (e.g., methyl, ethyl, propyl, isopropyl, butyl, pentyl, hexyl, etc.) having one or more halogen (e.g., chlorine, bromine, iodine or fluorine), and more preferably mono(or di or tri)-halo(lower)alkyl such as chloromethyl, bromomethyl, 2-iodoethyl, 2,2,2-trichloroethyl, 2,2,2-trifluoroethyl, 3-bromopropyl or the like.

Suitable lower unsaturated aliphatic group may include lower alkenyl (e.g., vinyl, allyl, isopropenyl, butenyl, pentenyl, hexenyl, etc.); lower alkynyl (e.g., ethynyl, propynyl, butynyl, pentynyl, hexynyl, etc.), and the like.

Suitable protected carboxy may include an esterified carboxy and the like, and suitable examples of the ester moiety in said esterified carboxy may be the ones such as lower alkyl ester (e.g., methyl ester, ethyl ester, propyl ester, isopropyl ester, butyl ester, isobutyl ester, pentyl ester, hexyl ester, 1-cyclopropylethyl ester, etc.) which may have at least one suitable substituent(s), for example, lower alkanoyloxy(lower)alkyl ester (e.g., acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, etc.), lower alkanesulfonyl(lower)alkyl ester (e.g., 2-mesylethyl ester, etc.) or mono(or di or tri)-halo(lower)alkyl ester (e.g., 2-iodoethyl ester, 2,2,2-trichloroethyl ester, etc.);

lower alkenyl ester (e.g., vinyl ester, allyl ester, etc.);

lower alkynyl ester (e.g., ethynyl ester, propynyl ester, etc.);

ar(lower)alkyl ester which may have at least one suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.); aryl ester which may have at least one suitable substituent(s) (e.g., phenyl ester, 4-chlorophenyl ester, tolyl ester, tertiarybutylphenyl ester, xylyl ester, mesityl ester, cumenyl ester, etc.), and the like.

Suitable protected amino may include an amino group substituted by a conventional protecting group such as acyl as mentioned below, ar(lower)alkyl which may have at least one suitable substituent(s) (e.g., benzyl, 4-methoxybenzyl, phenethyl, trityl, 3,4-dimethoxybenzyl, etc.) or the like.

Suitable acyl may include carbamoyl, aliphatic acyl group and acyl group containing an aromatic or heterocyclic ring. And, suitable examples of the said acyl may be lower alkanoyl (e.g., formyl, acetyl, propionyl, butyl, isobutyryl, valeryl, isovaleryl, oxalyl, succinyl, pivaloyl, etc.); lower alkoxycarbonyl (e.g., methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.);

lower alkanesulfonyl (e.g., mesyl, ethanesulfonyl, propanesulfonyl, isopropanesulfonyl, butanesulfonyl, etc.);

arenesulfonyl (e.g., benzenesulfonyl, tosyl, etc.); aroyl (e.g., benzoyl, toluoyl, naphthoyl, phthaloyl, indancarbonyl, etc.);

ar(lower)alkanoyl (e.g., phenylacetyl, phenylpropionyl, etc.);

ar(lower)alkoxycarbonyl (e.g., benzyloxycarbonyl, etc.), and the like.

The acyl moiety as stated above may have at least one suitable substituent(s) such as halogen (e.g., chlorine, bromine, iodine or fluorine), cyano, lower alkyl (e.g., methyl, ethyl, propyl, isopropyl, butyl, etc.), lower alkenyl (e.g., vinyl, allyl, etc.), or the like.

The processes for preparing the object compounds of the present invention are explained in detail in the following.

Process 1

The object compound (I) or a salt thereof can be prepared by reacting the compound (II) or its reactive derivative at the amino group or a salt thereof with the compound (III) or its reactive derivative at the carboxy group or salt thereof.

Suitable reactive derivative at the amino group of the compound (II) may include Schiff's base type imino or its tautomeric enamine type isomer formed by the reaction of the compound (II) with a carbonyl compound such as acetoacetic acid or the like; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorus acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g., benzoic acid, etc.); a symmetrical acid anhydride, an activated amide with imidazole, 4-substituted imidazole, dimethylpyrazole, triazole or tetrazole; or an activated ester (e.g., cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresylthioester, carboxymethyl thioester, pyranyl ester, piperidyl ester, 8-quinolyl thioester, etc.), or an ester with a N-hydroxy compound (e.g., N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N-carbonylbis(2-methylimidazole), pentamethyleneketene-N-cyclohexylimine, diphenylketene-N-cyclohexylimine, ethoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)isoxazolium hydroxide intra-molecular salt, (chloromethylene)dimethylammonium chloride, 1-(p-chlorobenzenesulfonyloxy)-6-chloro-1H-benzotriazole, or the like.

The reaction may also be carried out in the presence of an inorganic or organic base such as an alkali metal bicarbonate, tri(lower)alkylamine, pyridine, N-(lower)alkylmorphorine, N,N-di(lower)-alkylbenzylamine, or the like. The reaction temperature is not critical, and the reaction is usually carried out under cooling or at ambient temperature.

In the present reaction, syn isomer of the object compound (I) can be obtained preferably by conducting the present reaction of the compound (II) with the corresponding syn isomer of the starting compound (III), for example, in the presence of a Vilsmeier reagent prepared by the reaction of dimethylformamide with thionyl chloride, phosgene, phosphorus oxychloride, etc. and under around neutral condition.

Process 2

The object compound (Ia) or a salt thereof can be prepared by subjecting the compound (Ib) or a salt thereof to elimination reaction of the amino protective group.

Suitable salt of the comound (Ib) can be referred to the metal salt, ammonium salt and organic amine salt exemplified for the compound (II).

The elimination reaction is carried out in accordance with a conventional method such as hydrolysis, reduction, or the like. The hydrolysis may also include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, cycloalkoxycarbonyl, substituted or unsubstituted aralkoxycarbonyl, aralkyl (e.g., trityl), substituted phenylthio, substituted aralkylidene, substituted alkylidene, substituted cycloalkylidene or the like.

Suitable acid includes an organic or inorganic acid such as formic acid, trifluoroacetic acid, benzenesulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, etc. The acids can be selected according to the kind of the protected group to be eliminated. When the elimination reaction is conducted with an acid, it can be carried out in the presence or absence of a solvent. Suitable solvent includes water, a conventional organic solvent or a mixture thereof. The hydrolysis using hydrazine is commonly applied for eliminating a phthaloyl type amino-protective group.

The reductive elimination is generally applied for eliminating the protective group, for example, haloalkoxycarbonyl (e.g., trichloroethoxycarbonyl, etc.), substituted or unsubstituted aralkoxy carbonyl (e.g., benzyloxycarbonyl, etc.), 2-pyridylmethoxycarbonyl, etc.

Suitable reduction may include, for example, reduction with an alkali metal borohydride (e.g., sodium borohydride, etc.), reduction with a combination of a metal (e.g., tin, zinc, iron, etc.) or the said metal together with a metal salt compound (e.g., chromous chloride, chromous acetate, etc.) and an organic or inorganic acid (e.g., acetic acid, propionic acid, hydrochloric acid, etc.); and catalytic reduction. Suitable catalyst includes a conventional one, for example, Raney nickel, platinum oxide, palladium on charcoal and the like.

Among the protective groups, the acyl group can generally be eliminated by hydrolysis. Especially, trifluoroacetyl group can easily be eliminated by treating with water even in round neutral condition, and halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g., phosphorus oxychloride, etc.) and an iminoetherifying agent such as lower alkanol (e.g., methanol, ethanol, etc.), if necessary, followed by hydrolysis.

The reaction temperature is not critical and may suitably be selected in accordance with the kind of the protective group for the amino group and the eliminatiion method as mentioned above, and the reaction is preferably carried out under a mild condition such as under cooling or at slightly elevated temperature.

The present invention includes, within its scope, the cases that the protected carboxy is transformed into the free carboxy group during the reaction or the post-treating step of the present process.

The processes for preparing the starting compounds of the present invention are explained in detail in the following.

Method 1

The starting compounds (IIIa) or a salt thereof can be prepared by reacting the compound (IIIb) or its reactive derivative at the amino group or a salt thereof with a formylating agent.

Suitable reactive derivative at the amino group of the compound (IIIb) can be referred to the ones as illustrated for the compound (II) in Process 1.

Suitable formylating agent may include all conventional ones such as formic acid or its reactive derivative at the carboxy group (e.g., acid halide, acid anhydride, activated amide, activated ester, etc.).

The present reaction can be carried out in the similar manner to that illustrated in the reaction of Process 1.

Method 2.

The starting compound (IIIa) or a salt thereof can also be prepared by reacting the compound (IIIc) or a salt thereof with the compound (IV) or a salt thereof.

The present reaction is usually carried out in a a solvent such as water, a lower alkanol (e.g., methanol, ethanol, etc.) or any other solvent which does not adversely influence the reaction.

The present reactions preferably carried out in the presence of an inorganic or organic base as aforementioned in Process 1.

The reaction temperature is not critical and the reaction is usually carried out under cooling to heating.

The object compounds (I) and pharmaceutically acceptable salt thereof of the present invention exhibit high antibacterial activity and inhibit the growth of a number of microorganisms including Gram-positive and Gram-negative bacteria. Especially, the syn isomers of the object compounds (I) and pharmaceutically acceptable salt thereof exhibit generally much higher antibacterial activity than that of the corresponding anti isomers of the object compounds (I) and pharmaceutically acceptable salt thereof. For therapeutic purpose, the compounds according to the present invention can be used in the form of pharmaceutical preparation which contain said compounds, as an active ingredient, in admixture with a pharmaceutically acceptable carriers such as an organic or inorganic solid or liquid excipient suitable for oral, parenteral or external administration. The pharmaceutical preparations may be capsules, tablets, dragees, ointments or suppositories, solutions, suspensions, emulsions, and the like. If desired, there may be included in the above preparations auxiliary substances, stabilizing agents, wetting or emulsifying agents, buffers and other commonly used additives.

While the dosage of the compounds will vary depend upon the age and condition of the patient, an average single dose of about 10 mg., 50 mg., 100 mg., 250 mg., 500 mg., and 1000 mg. of the compounds according to the present invention was proved to be effective for treating infectious diseases caused by pathogenic bacteria.

In order to illustrate the usefulness of the object compounds, anti-microbial activities of some representative compounds of the present invention against some test strains of pathogenic bacteria are shown in their minimal inhibitory concentrations below.

Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound and the minimal inhibitory concentration (MIC) was expressed in terms of μg/ml. after incubation at 37° C. for 20 hours.

Test compounds (1) 2-Methyl-7-[2-(2-propynyloxyimino)-2-(2-aminothiazol-4-yl)acetamido]-3-cephem-4-carboxylic acid (syn isomer) (Test compound (1))

(2) 2-Methyl-7-[2-allyloxyimino-2-(2-aminothiazol-4-yl)acetamido]-3-cephem-4-carboxylic acid (syn isomer) (Test compound (2))

(3) 2-Methyl-7-[2-(2,2,2-trifluoroethoxyimino)-2-(2-aminothiazol-4-yl)acetamido]-3-cephem-4-carboxylic acid hydrochloride (syn isomer) (Test compound (3))

| Test Results: | | | | |
|---|---|---|---|---|
| | | Test compounds | | |
| Organism | | (1) | (2) | (3) |
| P. vulgaris | IAM-1025 | 0.05 | 0.39 | 0.1 |
| | No. 1 | 0.1 | 0.39 | 0.2 |
| | No. 2 | 0.1 | 0.39 | 0.78 |
| P. mirabilis | No. 1 | 0.1 | 0.39 | 0.78 |
| | No. 18 | 0.05 | 0.39 | 0.39 |

The present invention is illustrated by the following examples.

EXAMPLE 1

To dimethylformamide (0.4 g) was added dropwise phosphorus oxychloride (0.84 g) under stirring and ice-cooling, and the mixture was stirred for 30 minutes at 40° C. and then suspended in ethyl acetate (10 ml). To the suspension was added 2-(2-propynyloxyimino)-2-(2-formylaminothiazol-4-yl)acetic acid (syn isomer) (1.27 g) under stirring and ice-cooling and then stirred for 30 minutes under ice-cooling. Thus obtained solution was added to a solution, which was prepared by stirring a mixture of 2-methyl-7-amino-3-cephem-4-carboxylic acid (1.44 g) and trimethylsilylacetamide (5.2 g) in tetrahydrofuran (40 ml), under cooling to −25° C. The mixture was stirred for 1 hour at −20° C. to −10° C., and a saturated aqueous solution of sodium chloride (100 ml) was added thereto. Thus obtained mixture was adjusted to pH 7.5 with 20% aqueous solution of sodium carbonate, and the aqueous layer was separated. To the aqueous layer was added ethyl acetate, and adjusted to pH 2 with 10% hydrochloric acid, and then extracted with ethyl acetate. The ethyl acetate layer was washed with a saturated aqueous solution of sodium chloride, dried over magnesium sulfate and then evaporated. The residue was pulverized in diethyl ether, collected by filtration and then dried to give 2-methyl-7-[2-(2-propynyloxyimino)-2-(2-formylaminothiazol-4-yl)acetamido]-3-cephem-4-carboxylic acid (syn isomer) (2.2 g).

I.R. Spectrum (Nujol) 3250, 1780, 1670, 1630, 1540 cm$^{-1}$

N.M.R. Spectrum (d$_6$—DMSO, δ) 1.45 (3H, d, J=6 Hz), 3.50 (1H, m), 3.70 (1H, m), 4.78 (2H, d, J=2 Hz), 5.17 (1H, d, J=5 Hz), 5.93 (1H, dd, J=5 and 8 Hz), 6.58 (1H, d, J=6 Hz) 7.47 (1H, s), 8.57 (1H, s), 9.77 (1H, d, J=8 Hz), 12.38 (1H, broad s)

EXAMPLE 2

Similarly, the following compounds were obtained.
(1) 2-Methyl-7-[2-allyloxyimino-2-(2-formylaminothiazol-4-yl)acetamido]-3-cephem-4-carboxylic acid (syn isomer).

I.R. Spectrum (Nujol) 3150, 1790, 1730 (shoulder), 1680, 1635 (shoulder), 1550 cm$^{-1}$ N.M.R. Spectrum (d$_6$—DMSO, δ) 1.38 (3H, d, J=8 Hz), 3.77 (1H, m), 4.58 (1H, d, J=7 Hz), 5.10 (1H, d, J=4 Hz), 5.42 (1H, m), 5.67–6.27 (2H, m), 6.50 (1H, d, J=6 Hz), 7.33 (1H, s), 8.48 (1H, s), 9.67 (1H, d, J=8 Hz), 12.38 (1H, broad s)

(2) 2-Methyl-7-[2-(2,2,2,-trifluoroethoxyimino)-2-(2-formylaminothiazol-4-yl)acetamido]-3-cephem-4-carboxylic acid (syn isomer)

I.R. Spectrum (Nujol) 3250, 1780, 1680, 1630, 1540 cm$^{-1}$

N.M.R. Spectrum (d$_6$—DMSO, δ) 1.38 (3H, d, J=6 Hz), 3.78 (1H, m), 4.75 (2H, q, J=8.5 Hz), 5.13 (1H, d, J=5 Hz), 5.95 (1H, dd, J=5 and 8 Hz), 6.25 (1H, d, J=6 Hz), 7.50 (1H, s), 8.57 (1H, s), 9.90 (1H, d, J=8 Hz), 12.77 (1H, broad s)

(3) 2-Methyl-7-[2-(2-propynyloxyimino)-2-(2-aminothiazol-4-yl)acetamido]-3-cephem-4-carboxylic acid (syn isomer)

I.R. Spectrum (Nujol) 3300, 1780, 1670, 1630, 1540 cm$^{-1}$ (4) 2-Methyl-7-[2-allyloxyimino-2-(2-aminothiazol-4-yl)acetamido]-3-cephem-4-carboxylic acid (syn isomer)

I.R. Spectrum (Nujol) 3320, 1785, 1665, 1630, 1550 cm$^{-1}$ (5) 2-Methyl-7-[2-(2,2,2-trifluoroethoxyimino)-2-(2-aminothiazol-4-yl)acetamido]-3-cephem-4-carboxylic acid hydrochloride (syn isomer)

I.R. Spectrum (Nujol) 3350, 3100, 1780, 1735, 1665, 1645, 1600, 1540 cm$^{-1}$

EXAMPLE 3

To a suspension of 2-methyl-7-[2-(2-propynyloxyimino)-2-(2-formylaminothiazol-4-yl)acetamido]-3-cephem-4-carboxylic acid (syn isomer) (2.1 g) in methanol (42 ml) was added concentrated hydrochloric acid (0.97 ml), and the mixture was stirred for 2 hours at ambient temperature. The methanol was distilled off from the reaction mixture, and the residue was dissolved in water (50 ml) and then filtered. The filtrate was adjusted to pH 3 with a saturated aqueous solution of sodium bicarbonate, and the precipitates were collected by filtration and then dried to give 2-methyl-7-[2-(2-propynyloxyimino)-2-(2-aminothiazol-4-yl)acetamido]-3-cephem-4-carboxylic acid (syn isomer) (0.6 g).

I.R. Spectrum (Nujol)
3300, 1780, 1670, 1630, 1540 cm$^{-1}$

N.M.R. Spectrum (d$_6$—DMSO, δ) 1.48 (3H, d, J=6 Hz), 3.55 (1H, m), 3.77 (1H, m), 4.77 (2H, d, J=2 Hz), 5.17 (1H, d, J=5 Hz), 5.90 (1H, dd, J=5 and 8 Hz), 6.60 (1H, d, J=6 Hz), 6.85 (1H, s), 9.75 (1H, d, J=8 Hz)

EXAMPLE 4

A mixture of 2-methyl-7-[2-(2,2,2-trifluoroethoxyimino)-2-(2-formylaminothiazol-4-yl)acetamido]-3-cephem-4-carboxylic acid (syn isomer) (0.8 g), concentrated hydrochloric acid (0.51 ml) and methanol (16 ml) was stirred for 2 hours at ambient temperature, and then evaporated. Thus obtained pale yellow residue was pulverized in diethyl ether, collected by filtration and then dried to give 2-methyl-7-[2-(2,2,2-trifluoroethoxyimino)-2-(2-aminothiazol-4-yl)acetamido]-3-cephem-4-carboxylic acid hydrochloride (syn isomer) (0.8 g).

I.R. Spectrum (Nujol) 3350, 3100, 1780, 1735, 1665, 1645, 1600, 1540 cm$^{-1}$

N.M.R. Spectrum (d$_6$—DMSO, δ) 1.43 (3H, d, J=6 Hz), 3.82 (1H, m), 4.80 (2H, q, J=8.5 Hz), 5.15 (1H, d, J=5 Hz), 5.90 (1H, dd, J=5 and 8 Hz), 6.60 (1H, d, J=6 Hz), 7.05 (1H, s), 9.93 (1H, d, J=8 Hz)

EXAMPLE 5

2-methyl-7-[2-allyloxyimino-2-(2-aminothiazol-4-yl)acetamido]-3-cephem-4-carboxylic acid (syn isomer) was obtained according to the similar manner to that of Example 3.

I.R. Spectrum (Nujol) 3320, 1785, 1665, 1630, 1550 cm$^{-1}$

N.M.R. Spectrum (d$_6$—DMSO, δ) 1.42 (3H, d, J=6 Hz), 3.80 (1H, m), 4.60 (2H, d, J=5 Hz), 5.12 (1H, d, J=4 Hz), 5.10–5.48 (2H, m), 5.90 (1H, dd, J=4 and 8 Hz), 5.64–6.20 (1H, m), 6.58 (1H, d, J=6 Hz), 6.76 (1H, s), 7.28 (2H, m), 9.66 (1H, d, J=8 Hz)

Preparation of the starting compounds (III)

Preparation 1

A suspension of 2-(2-formylaminothiazol-4-yl)-glyoxylic acid (3.0 g) in methanol (60 ml) and water (60 ml) was adjusted to pH 8 with 1 N aqueous solution of sodium hydroxide under stirring. To the solution was added 2,2,2-trifluoroethoxyamine hydrochloride (2.24 g) and then adjusted to pH 2.5 to 3 with 1 N aqueous solution of sodium hydroxide. After the solution was stirred at ambient temperature for 1.5 hours, methanol was removed from the resultant solution under reduced pressure. The remaining aqueous solution was adjusted to pH 7 with 1 N aqueous solution of sodium hydroxide and then washed with ethyl acetate. To the aqueous solution was added ethyl acetate and then adjusted to pH 1.5 with 10% hydrochloric acid, and then extracted with ethyl acetate. The extract was washed with a saturated aqueous solution of sodium chloride, dried over magnesium sulfate and then evaporated under reduced pressure to give 2-(2,2,2-trifluoroethoxyimino)-2-(2-formylaminothiazol-4-yl)acetic acid (syn isomer) (2.4 g), mp 162° to 163° C. (dec.).

I.R. Spectrum (Nujol) 3200, 1700, 1600, 1560 cm$^{-1}$

Preparation 2

(1) Ethyl 2-(2-propynyloxyimino)-3-oxobutyrate (syn isomer) (71.2 g) was obtained by reacting ethyl 2-hydroxyimino-3-oxobutyrate (syn isomer) (56.7 g) with 2-propynyl bromide (43 g) in the presence of potassium carbonate (72.3 g) and N,N-dimethylformamide (280 ml).

I.R. Spectrum (Film) 3280, 3220, 2120, 1735, 1670 cm$^{-1}$ (2) Ethyl 2-(2-propynyloxyimino)-3-oxo-4-chlorobutyrate (syn isomer) (61.6 g) was obtained by reacting ethyl 2-(2-propynyloxyimino)-3-oxobutyrate (syn isomer) (71.2 g) with sulfuryl chloride (50.2 g) in acetic acid (81 ml).

I.R. Spectrum (Film) 3300, 2130, 1745, 1720, 1675 cm$^{-1}$ (3) Ethyl 2-(2-propynyloxyimino)-2-(2-aminothiazol-4-yl)acetate (syn isomer) (35.6 g) was obtained by reacting ethyl 2-(2-propynyloxyimino)-3-oxo-4-chlorobutyrate (syn isomer) (61 g) with thiourea (20 g) in the presence of sodium acetate trihydrate (35.8 g), water (150 ml) and ethanol (180 ml).

I.R. Spectrum (Nujol) 3290, 2220, 1729 cm$^{-1}$ (4) 2-(2-propynyloxyimino)-2-(2-aminothiazol-4-yl)acetic acid (syn isomer) (1.924 g) was obtained by hydrolyzing ethyl 2-(2-propynyloxyimino)-2-(2-aminothiazol-4-yl)-acetate (syn isomer) (2.8 g) in the presence of 1 N aqueous solution of sodium hydroxide (22.17 ml), methanol (23 ml) and tetrahydrofuran (20 ml).

I.R. Spectrum (Nujol) 2190, 1740 cm$^{-1}$

Preparation 3

Formic acid (107 g) was added to acetic anhydride (239 g) under ice-cooling, and the mixture was stirred for 1 hour at 50° C. and then cooled to 20° C. To the mixture was added 2-(2-propynyloxyimino)-2-(2-aminothiazol-4-yl)acetic acid (syn isomer) (135 g), and the mixture was stirred for 3 hours at ambient temperature. To the mixture was added diisopropyl ether (400 ml) and then the precipitated crystals were collected by filtration, washed with diisopropyl ether and then dried to give 2-(2-propynyloxyimino)-2-(2-formylaminothiazol-4-yl)acetic acid (syn isomer) (118.4 g).

I.R. Spectrum (Nujol) 3250, 2130, 1685, 1600, 1560 cm$^{-1}$

N.M.R. Spectrum d$_6$—DMSO, δ) 3.53 (1H, m), 4.87 (2H, d, J=2 Hz), 7.63 (1H, s), 8.61 (1H, s), 12.7 (1H, broad s)

Preparation 4

To a solution of 2-(2-formylaminothiazol-4-yl)-glyoxylic acid (30 g) and sodium bicarbonate (12.6 g) in water (1300 ml) was added allyloxyamine hydrochloride (19.8 g), and the mixture was stirred for 7 hours at ambient temperature at pH 6. To the reaction mixture was added ethyl acetate (500 ml). After the mixture was adjusted to pH 1.9 with 10% hydrochloric acid, the ethyl acetate layer was separated. The ethyl acetate layer was washed with an aqueous solution of sodium chloride, dried over magnesium sulfate and then the solvent was distilled off. The residue was pulverized in diisopropyl ether, collected by filtration and then dried to give 2-allyloxyimino-2-(2-formylaminothiazol-4-yl)acetic acid (syn isomer) (25.3 g).

I.R. Spectrum (Nujol) 3110, 1730, 1660, 1540 cm$^{-1}$
N.M.R. Spectrum d$_6$—DMSO, δ) 4.70 (2H, m), 5.13–5.60 (2H, m), 5.73–6.27 (1H, m), 7.57 (1H, s), 8.35 (1H, s)

The other starting compounds (III) can be prepared according to the similar manners to those of Preparations 1 to 4.

What is claimed is:

1. A compound of the formula:

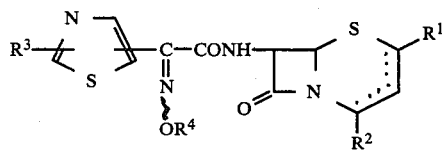

wherein R$^1$ is lower alkyl of 1–6 carbon atoms, R$^2$ is carboxy or protected carboxy, R$^3$ is amino or protected amino, and R$^4$ is C$_1$–C$_6$ alkynyl, C$_1$–C$_6$ alkynyl or C$_1$–C$_6$ alkyl having at least one fluorine, chlorine, bromine or iodine substituent and pharmaceutically acceptable salts thereof.

2. The compound of claim 1,
which is syn isomer.

3. The compound of claim 2, wherein R$^1$ is lower alkyl, R$^2$ is carboxy, R$^3$ is amino or amino protected by a carbamoyl, aliphatic acyl, aromatic acyl or heterocyclic acyl substituent, and R$^4$ is trihalo(C$_1$–C$_6$)alkyl, C$_1$–C$_6$ alkenyl or C$_1$–C$_6$ alkynyl.

4. The compound of claim 3,
wherein R$^3$ is amino.

5. The compound of claim 4,
which is 2-methyl-7-[2-(2,2,2-trifluoroethoxyimino)-2-(2-aminothiazol-4-yl)acetamido]-3-cephem-4-carboxylic acid (syn isomer) or its hydrochloride.

6. The compound of claim 4,
which is 2-methyl-7-[2-allyloxyimino-2-(2-aminothiazol-4-yl)acetamido]-3-cephem-4-carboxylic acid (syn isomer).

7. The compound of claim 4,
which is 2-methyl-7-[2-(2-propynyloxyimino)-2-(2-aminothiazol-4-yl)acetamido]-3-cephem-4-carboxylic acid (syn isomer).

8. The compound of claim 3,
wherein R$^3$ is lower alkanoylamino.

9. An antibacterial pharmaceutical composition comprising the compound of claim 1 and a pharmaceutically acceptable, substantially non-toxic carrier or excipient.

UNITED STATES PATENT AND TRADEMARK OFFICE
CERTIFICATE OF CORRECTION

PATENT NO. : 4,305,937
DATED : December 15, 1981
INVENTOR(S) : TAKASHI KAMIYA ET AL It is certified that error appears in the above—identified patent and that said Letters Patent is hereby corrected as shown below:

Column 13, line 31, change "alkynyl" (first occurrence) to --alkenyl--.

Signed and Sealed this

First Day of June 1982

[SEAL]

Attest:

GERALD J. MOSSINGHOFF

Attesting Officer      Commissioner of Patents and Trademarks